US00PP15616P2

(12) United States Plant Patent
Hanes

(10) Patent No.: US PP15,616 P2
(45) Date of Patent: Mar. 1, 2005

(54) ***GERANIUM* PLANT NAMED 'CANTE DEREDS'**

(50) Latin Name: *Pelargonium×hortorum×Pelargonium tongaense*
Varietal Denomination: Cante Dereds

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,518

(22) Filed: Apr. 5, 2004

(51) Int. Cl.[7] ..... A01H 5/00
(52) U.S. Cl. ..... Plt./324
(58) Field of Search ..... Plt./324

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Geranium* plant named 'Cante Dereds', characterized by its upright, outwardly spreading and mounded growth habit; freely basal branching habit; dark green-colored leaves; freely flowering habit with many flower umbels per plant; flower umbels with numerous dark crimson red-colored single flowers; and resistance to leaf oedema.

1 Drawing Sheet

Botanical classification/cultivar designation: *Pelargonium×hortorum×Pelargonium tongaense* cultivar Cante Dereds.

BACKGROUND OF THE INVENTION

The present invention relates to a new and distinct cultivar of *Geranium* plant, botanically known as *Pelargonium×hortorum×Pelargonium tongaense,* commercially known as an interspecific *Geranium*, and hereinafter referred to by the name 'Cante Dereds'.

The new *Geranium* is a product of a planned breeding program conducted by the Inventor in Gilroy, Calif. The objective of the breeding program is to develop new *Geranium* cultivars with mounded plant habit, good basal branching, large flowers, attractive flower and foliage coloration and resistance to leaf oedema.

The new *Geranium* originated from a cross-pollination made by the Inventor in April, 2000 of a proprietary *Pelargonium×hortorum×Pelargonium tongaense* selection identified as code number 8738-3, not patented, as the female, or seed, parent with a proprietary *Pelargonium×hortorum×Pelargonium tongaense* selection identified as code number 8756-2, not patented, as the male, or pollen, parent. The cultivar Cante Dereds was discovered and selected by the Inventor as a flowering plant within the progeny from this cross-pollination in a controlled environment in Gilroy, Calif. in September, 2000.

Asexual reproduction of the new cultivar by terminal cuttings at Gilroy, Calif., since September, 2000 has shown that the unique features of this new *Geranium* are stable and reproduced true to type in successive generations of asexual reproduction.

SUMMARY OF THE INVENTION

The following traits have been repeatedly observed and are determined to be the unique characteristics of 'Cante Dereds'. These characteristics in combination distinguish 'Cante Dereds' as a new and distinct *Geranium* cultivar:

1. Upright, outwardly spreading and mounded growth habit.
2. Freely basal branching habit.
3. Dark green-colored leaves.
4. Freely flowering habit with many flower umbels per plant.
5. Flower umbels with numerous dark crimson red-colored single flowers.
6. Resistant to leaf oedema.

In side-by-side comparisons conducted in Gilroy, Calif., plants of the new *Geranium* differed from plants of the female parent selection in the following characteristics:

1. Plants of the new *Geranium* were more freely basal branching than plants of the female parent selection.
2. Plants of the new *Geranium* had lighter green-colored leaves than plants of the female parent selection.

In side-by-side comparisons conducted in Gilroy, Calif., plants of the new *Geranium* differed from plants of the male parent selection in the following characteristics:

1. Plants of the new *Geranium* flowered earlier than plants of the male parent selection.
2. Plants of the new *Geranium* had single flowers whereas plants of the male parent selection had semi-double flowers.

The new *Geranium* can be compared to the cultivar, Galleria Ruby Red, not patented. However, in side-by-side comparisons conducted in Gilroy, Calif., plants of the new *Geranium* differed from plants of the cultivar Galleria Ruby Red in the following characteristics:

1. Plants of the new *Geranium* had darker green-colored leaves than plants of the cultivar Galleria Ruby Red.
2. Plants of the new *Geranium* had darker colored pedicels than plants of the cultivar Galleria Ruby Red.
3. Flowers of plants of the new *Geranium* were single whereas flowers of plants of the cultivar Galleria Ruby Red were semi-double.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Cante Dereds'.

The photograph at the bottom of the sheet is a close-up view of typical flowers, flower buds and leaves of 'Cante Dereds'.

Flower and foliage colors in the photographs may differ slightly from the color values cited in the detailed botanical description which accurately describe the colors of the new *Geranium.*

DETAILED BOTANICAL DESCRIPTION

Plants of the cultivar Cante Dereds have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the late spring with day temperatures about 27 to 29° C., night temperatures about 16 to 18° C. and light levels about 2,000 foot-candles. Plants used for the photographs and description were about five months from planting rooted cuttings. In the following description, color references are made to The Royal Horticultural Society Colour Chart, 1995 Edition, except where general terms of ordinary dictionary significance are used.

Botanical classification: *Pelargonium×hortorum×Pelargonium tongaense* cultivar Cante Dereds.

Parentage:

*Female parent.*—Proprietary *Pelargonium×hortorum×Pelargonium tongaense* selection identified as code number 8738-3, not patented.

*Male parent.*—Proprietary *Pelargonium×hortorum×Pelargonium tongaense* selection identified as code number 8756-2, not patented.

Propagation:

*Type cutting.*—Terminal cuttings.

*Time to initiate roots.*—About 12 to 14 days at 22° C.

*Time to develop roots.*—About 25 to 30 days at 22° C.

*Root description.*—Fibrous; white in color.

*Rooting habit.*—Freely branching.

Plant description:

*General appearance.*—Upright, outwardly spreading and mounded growth habit.

*Growth and branching habit.*—Vigorous and very freely basal branching with about twelve lateral branches per plant. Pinching, that is, removal of terminal apices, is typically not required.

*Plant height to top of foliage.*—About 19 cm.

*Plant height to top of flower umbels.*—About 24 cm.

*Plant width.*—About 55 cm.

*Lateral branches.*—Length: About 30 cm. Diameter: About 6 mm. Internode length: About 3.5 cm. Texture: Pubescent. Color: 144A.

*Foliage description.*—Arrangement: Alternate, simple; after flowering, opposite. Length: About 7.5 cm. Width: About 8.5 cm. Shape: Rounded reniform. Apex: Rounded. Base: Cordate. Margin: Crenate with about seven shallow lobes. Venation: Palmate. Texture, upper and lower surfaces: Slightly coarse; glandular; pubescent. Color: Developing foliage, upper surface: 146A. Developing foliage, lower surface: 147B. Fully expanded foliage, upper surface: 147A. Fully expanded foliage, lower surface: 147B. Venation, upper surface: 146C. Venation, lower surface: 147C. Petiole: Length: About 12 cm. Diameter: About 2 mm. Texture, upper and lower surfaces: Pubescent. Color, upper and lower surfaces: 146A.

Flower description:

*Flower arrangement and type.*—Single rounded flowers arranged in hemispherical umbels arising from apical leaf axils. Umbels displayed above the foliage. At full flowering, usually about 25 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 5 cm. Diameter: About 9 cm. Number of flowers and flower buds per umbel: About 26. Flower diameter: About 4 cm. Flower depth (height): About 2.5 cm.

*Flower buds.*—Length: About 1.4 cm. Diameter: About 6 mm. Shape: Ovoid. Color: 185A.

*Petals.*—Quantity/arrangement: About five petals per flower in a single whorl. Length: About 2.3 cm. Width, upper two petals: About 1.4 cm. Width, lower three petals: About 1.6 cm. Shape: Obovate to slightly spatulate. Apex: Rounded. Base: Attenuate. Margin: Entire. Texture, upper and lower surfaces: Smooth; satiny. Color: When opening, upper surface: Brighter and more saturated than 46A. When opening, lower surface: Brighter than 53B. Fully opened, upper two petals, upper surface: More crimson red than 45A; at the base, 155D; venation, 185A. Fully opened, lower three petals, upper surface: More crimson red than 45A; at the base, 155D; venation, similar to petal color. Fully opened, upper two petals, lower surface: Brighter than 53B; at the base, 155D; venation, 185A. Fully opened, lower three petals, lower surface: Brighter than 53B; at the base, 155D; venation, similar to petal color.

*Sepals.*—Quantity/arrangement: Five per flower in a single whorl; not imbricate on open flowers. Length: About 1.3 cm. Width: About 3 mm. Shape: Elliptical. Apex: Acuminate. Margin: Entire. Texture, upper and lower surfaces: Smooth, glabrous. Color, upper and lower surfaces: 144A.

*Peduncle* (*umbel stem*).—Length: About 17 cm. Diameter: About 3 mm. Angle: About 45° from vertical. Strength: Strong. Texture: Pubescent. Color: 144A.

*Pedicel* (*individual flower stem*).—Length: About 2.7 cm. Diameter: About 1 mm. Angle: About 20 to 45° from vertical. Strength: Strong. Texture: Pubescent. Color: 144A.

*Reproductive organs.*—Androecium: Anther quantity: About six to ten per flower. Anther size: About 1 by 2 mm. Anther shape: Oval. Anther color: 53A. Pollen amount: Scarce. Pollen color: 171B. Gynoecium: Pistil quantity: One per flower. Pistil length: About 9 mm. Stigma shape: Five-parted, star-shaped; reflexed. Stigma color: 53B. Style length: About 1.5 mm. Style color: 158A. Ovary color: 194C.

*Seed/fruit.*—Seed and fruit development has not been observed.

Disease/pest resistance: Resistance to pathogens and pests common to *Pelargonium* has not been observed.

Oedema resistance: Plants of the new *Geranium* have been observed to be resistant to leaf oedema when exposed to conditions conducive to leaf oedema development.

It is claimed:

1. A new and distinct cultivar of *Geranium* plant named 'Cante Dereds', as herein illustrated and described.

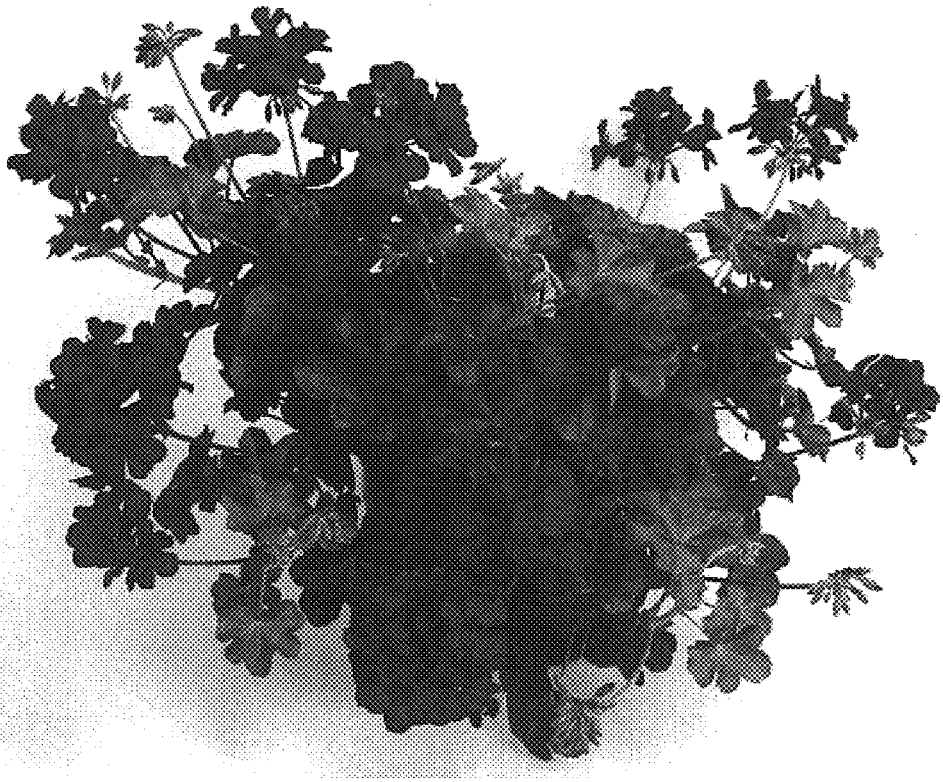
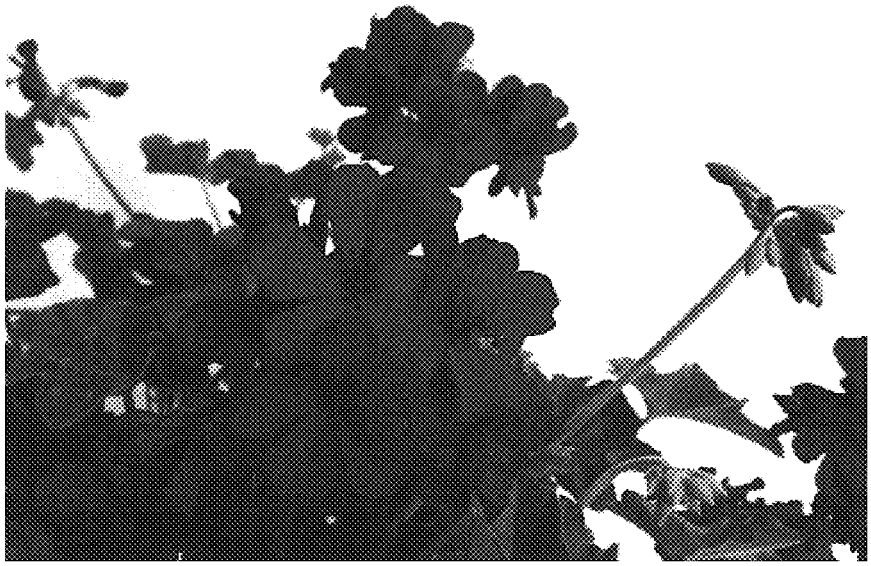

* * * * *